US010017470B2

(12) United States Patent
Gambhire et al.

(10) Patent No.: US 10,017,470 B2
(45) Date of Patent: Jul. 10, 2018

(54) TREATMENT FOR LIPODYSTROPHY

(75) Inventors: Dhiraj Gambhire, Gujarat (IN); Rajendrakumar Hariprasad Jani, Gujarat (IN); Bipin Pandey, Gujarat (IN); Kaushik Sata, Gujarat (IN); Himanshu Kothari, Gujarat (IN); Pankaj Ramanbhai Patel, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 286 days.

(21) Appl. No.: 13/978,791

(22) PCT Filed: Jan. 30, 2012

(86) PCT No.: PCT/IN2012/000069
§ 371 (c)(1),
(2), (4) Date: Sep. 4, 2013

(87) PCT Pub. No.: WO2012/104869
PCT Pub. Date: Aug. 9, 2012

(65) Prior Publication Data
US 2013/0338209 A1 Dec. 19, 2013

(30) Foreign Application Priority Data
Jan. 31, 2011 (IN) .......................... 257/MUM/2011

(51) Int. Cl.
C07D 207/33 (2006.01)
A61K 31/40 (2006.01)
C07D 207/333 (2006.01)
A61K 45/06 (2006.01)
A61K 9/20 (2006.01)

(52) U.S. Cl.
CPC .......... *C07D 207/333* (2013.01); *A61K 31/40* (2013.01); *A61K 45/06* (2013.01); *A61K 9/2009* (2013.01); *A61K 9/2013* (2013.01)

(58) Field of Classification Search
CPC .... C07D 207/333; A61K 31/40; A61K 45/06; A61K 9/2009; A61K 9/2013
See application file for complete search history.

(56) References Cited

U.S. PATENT DOCUMENTS

| 4,231,938 A | 11/1980 | Monaghan et al. |
| 4,346,227 A | 8/1982 | Terahara et al. |
| 4,444,784 A | 4/1984 | Hoffman et al. |
| 5,273,995 A | 12/1993 | Roth |
| 5,354,772 A | 10/1994 | Kathawala |
| 6,166,063 A | 12/2000 | Villhauer |
| 6,395,767 B2 | 5/2002 | Robl et al. |
| 6,699,871 B2 | 3/2004 | Edmondson et al. |
| 6,987,123 B2 | 1/2006 | Lohray et al. |
| 7,041,837 B2 | 5/2006 | Lohray et al. |
| 7,323,491 B2 | 1/2008 | Lohray et al. |
| 7,407,955 B2 | 8/2008 | Himmelsbach et al. |
| 8,110,598 B2 | 2/2012 | Lohray et al. |
| 8,212,057 B2 | 7/2012 | Lohray et al. |
| 8,558,009 B2 | 10/2013 | Lohray et al. |
| 8,772,342 B2 | 7/2014 | Darteil et al. |
| 2003/0199498 A1 | 10/2003 | Lohray et al. |
| 2003/0236254 A1* | 12/2003 | Lohray .............. C07D 207/325 514/227.8 |
| 2007/0238776 A1 | 10/2007 | Lohray et al. |
| 2011/0275669 A1 | 11/2011 | Lohray et al. |
| 2012/0121729 A1 | 5/2012 | Paterson et al. |
| 2013/0338209 A1 | 12/2013 | Gambhire et al. |
| 2016/0068484 A1 | 3/2016 | Jain et al. |
| 2016/0107989 A1 | 4/2016 | Dwivedi et al. |
| 2016/0136131 A1 | 5/2016 | Patel et al. |
| 2016/0166539 A1 | 6/2016 | Patel et al. |
| 2016/0194280 A1 | 7/2016 | Dwivedi et al. |
| 2016/0207884 A1 | 7/2016 | Dwivedi et al. |

FOREIGN PATENT DOCUMENTS

| EP | 1586571 A1 | 10/2005 |
| IN | 1910/MUM/2013 | 12/2014 |
| WO | WO-91/19702 A1 | 12/1991 |
| WO | WO-94/01420 A1 | 1/1994 |
| WO | WO-94/13650 A1 | 6/1994 |
| WO | WO-95/03038 A1 | 2/1995 |
| WO | WO-95/17394 A1 | 6/1995 |
| WO | WO-96/04260 A1 | 2/1996 |
| WO | WO-96/04261 A1 | 2/1996 |

(Continued)

OTHER PUBLICATIONS

Jeroen P.H. van Wijk, MD; Eelco J.P. de Koning, MD, PhD; Manuel Castro Cabezas, MD, PhD; Jos op't Roodt, BSc; Jorge Joven, MD, PhD;Ton J. Rabelink, MD, PhD; and Andy I. Hoepelman, MD, PhD, Comparison of Rosiglitazone and Metformin for Treating HIV Lipodystrophy a Randomized Trial, Ann Intern Med. 2005;143(5):337-346.*
Colleen Hadigan, MD, MPH; Sigal Yawetz, MD; Abraham Thomas, MD; Fiona Havers, MA; Paul E. Sax, MD; and Steven Grinspoon, MD, Metabolic Effects of Rosiglitazone in HIV Lipodystrophy, A Randomized, Controlled Trial, Ann Intern Med. 2004;140(10):788-794.*
Derek C. Macallan, Christine Baldwin, Sundihya Mandalia, Vjera Pandol-Kaljeyic, Nadine Higgins, Alan Grundy & Graeme J. Moyle, Treatment of Altered Body Composition in HIV Associated Lipodystrophy: Comparison of Rosiglitazone, Pravastatin, and Recombinant Human Growth Hormone, HIV Clinical Trials vol. 9, Issue 4, 2008.*
Marisa Tungsiripata,1, Dalia El Bejjanib,c,1, Nesrine Rizkc, Mary Ann O'Riordanc, Allison C. Rossc, Corrilynn Hilemanc, Norma Storerc, Danielle Harrillc and Grace A. McComseyc, Rosiglitazone improves lipoatrophy in patients receiving thymidine-sparing regimens, AIDS 2010, 24:1291-1298.*
International Preliminary Report on Patentability in PCT/IN2012/000069 dated Aug. 15, 2013.
International Search Report for PCT/IN2012/000069 dated May 9, 2012.
U.S. Appl. No. 15/345,035, Treatment for Lipodystrophy, filed Nov. 7, 2016.

(Continued)

*Primary Examiner* — Sarah Pihonak
*Assistant Examiner* — Jason Deck
(74) *Attorney, Agent, or Firm* — Goodwin Procter LLP

(57) ABSTRACT

The present invention provides a therapeutic compound of formula (I) and their pharmaceutically acceptable salts for the prevention and treatment of lipodystrophy caused because of HIV infection or combination therapy of HIV-1 protease inhibitors (Pis) and/or reverse transcriptase inhibitors (nRTIs) by neutralizing lipohypertrophy, lipoatrophy and metabolic abnormalities in HIV patient.

4 Claims, No Drawings

(56) References Cited

FOREIGN PATENT DOCUMENTS

| WO | WO-96/33998 A1 | 10/1996 |
| WO | WO-97/25042 A1 | 7/1997 |
| WO | WO-97/36579 A1 | 10/1997 |
| WO | WO-99/08501 A2 | 2/1999 |
| WO | WO-99/16758 A1 | 4/1999 |
| WO | WO-99/19313 A1 | 4/1999 |
| WO | WO-99/20614 A1 | 4/1999 |
| WO | WO-00/23417 A1 | 4/2000 |
| WO | WO-00/23445 A1 | 4/2000 |
| WO | WO-00/23451 A1 | 4/2000 |
| WO | WO-01/53257 A2 | 7/2001 |
| WO | WO-02/24625 A2 | 3/2002 |
| WO | WO 03009841 A1 * | 2/2003 |
| WO | WO 03/009841 | 6/2003 |
| WO | WO-2005/031335 A1 | 4/2005 |
| WO | WO-2012/104869 A1 | 8/2012 |
| WO | WO-2014/174524 A1 | 10/2014 |
| WO | WO-2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |

OTHER PUBLICATIONS

U.S. Appl. No. 14/782,609, A Novel Composition for Nonalcoholic Fatty Liver Disease (NAFLD), filed Oct. 6, 2015.

U.S. Appl. No. 15/343,859, Novel Composition for Nonalcoholic Fatty Liver Disease (NAFLD), filed Nov. 4, 2016.

U.S. Appl. No. 14/899,912, Formula Comprising a Hypolipidemic Agent, filed Dec. 18, 2015.

U.S. Appl. No. 14/783,336, Synergistic Compositions, filed Oct. 8, 2015.

U.S. Appl. No. 14/916,402, Improved Process for the Preparation of Pyrrole Derivatives, filed Mar. 3, 2016.

U.S. Appl. No. 14/894,744, A Process for Preparation of Pyrroles Having Hypolipidemic Hypocholesteremic Activities, filed Nov. 30, 2015.

U.S. Appl. No. 15/366,229, A Process for Preparation of Pyrroles Having Hypolipidemic Hypocholesteremic Activities, filed Dec. 1, 2016.

U.S. Appl. No. 14/915,457, Polymorphic Form of Pyrrole Derivative and Intermediate Thereof, filed Feb. 29, 2016.

International Search Report and Written Opinion dated Feb. 2, 2015 for International Patent Application No. PCT/IN2014/000367 (14 pages).

Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* (2013) vol. 33, pp. 809-816.

Brenna, E. et al. "Enzyme-mediated synthesis of EEHP and EMHP, useful pharmaceutical intermediates of PPAR agonists" *Tetrahedron: Asymmetry* (2009) vol. 20, pp. 2594-2599.

International Search Report and Written Opinion dated Mar. 23, 2015 for Application No. PCT/IN2014/000584 (14 pages).

International Search Report and Written Opinion dated Dec. 19, 2014 for Application No. PCT/IN2014/000551 (11 pages).

Demuth, H.-U. et al. "Type 2 diabetes—Therapy with dipeptidyl peptidase IV inhibitors," *Biochim. Biophys. Acta*, 1751 (2005) pp. 33-44.

Augustyns, K. et al. "Inhibitors of proline-specific dipeptidyl peptidases: DPP IV inhibitors as a novel approach for the treatment of Type 2 diabetes," *Expert Opin. Ther. Patents*, (2005) vol. 15, No. 10, pp. 1387-1407.

Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (Press V)." *J. Diabetes Sci. Technol.* (2014) vol. 8, No. 1, pp. 132-141.

Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (Press VI)," *Diabetes Technology & Therapeutics*, (2014) vol. 16, No. 2, pp. 63-71.

International Search Report and Written Opinion dated Dec. 23, 2014 for International Patent Application No. PCT/IN2014/000445 (10 pages).

International Preliminary Report on Patentability dated Oct. 6, 2015 for International Patent Application No. PCT/IN2014/000445 (7 pages).

Ansel et al. "Pharmaceutical Dosage Forms and Drug Delivery Systems, Seventh Edition" 1999, pp. 88-92.

Cairns, D. (editor) "Essentials of Pharmaceutical Chemistry, Fourth Edition" 2012, p. 14.

Bharate, S. et al. "Interactions and incompatibilities of pharmaceutical excipients with active pharmaceutical ingredients: a comprehensive review." *J. Excipient and Food Chem.* (2010) vol. 1, No. 3, pp. 3-26.

International Search Report and Written Opinion dated Nov. 20, 2014 for International Application No. PCT/IN2014/000489 (10 pages).

International Preliminary Report on Patentability dated Oct. 9, 2015 for International Application No. PCT/IN2014/000489 (7 pages).

Response to Written Opinion filed on May 21, 2015 for International Application No. PCT/IN2014/000489 (6 pages).

"Sodium Stearyl Fumarate", obtained on Jun. 23, 2015. Retrieved from the Internet: <URL: https://www.medicinescomplete.com/me/excipients/current/ . . . >, 4 pages.

Lieberman, et al. "Pharmaceutical Dosage Forms: Tablets, vol. 1, 2nd Edition" (1989) Marcel Dekker Inc., pp. 111-114.

Gennaro et al. "Remington's Pharmaceutical Sciences, 19th Edition" (1995) Mack Publishing, pp. 1380-1383.

Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.

International Search Report and Written Opinion dated Nov. 20, 2013 for International Application No. PCT/IN2013/000391 (13 pages).

International Preliminary Report on Patentability dated Jul. 9, 2015 for International Application No. PCT/IN2013/000391 (9 pages).

IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).

Anonymous "IND Minutes draft Jul. 19, 2012" Retrieved on Oct. 15, 2013 from the Internet from URL: http://www.docstoc.com/docs/145152750/IND-Minutes-draft-19-07-12 (1 page).

Anonymous "Lipaglyn™ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).

Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," *Diabetes* (2009) vol. 58, No. Suppl. 1, p. A569.

Ramirez, T. et al. "Structural Correlates of PPAR Agonist Rescue of Experimental Chronic Alcohol-Induced Steatohepatitis," *J. Clin. Exper. Pathology* (2012) vol. 2, No. 4, pp. 1-9.

Seo, Y. S. et al. "PPAR agonists treatment is effective in a nonalcoholic fatty liver disease animal model by modulating fatty-acid metabolic enzymes" *J. Gatroenterology Hepatology* (2008) vol. 23, No. 1, pp. 102-109.

Fan, W. and Evans, R. "PPARs and ERRs: molecular mediators of mitochondrial metabolism" *Curr. Opin. Cell Bio.* (2015) vol. 33, pp. 49-54.

(56) References Cited

OTHER PUBLICATIONS

LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.

Written Opinion of the International Searching Authority dated May 9, 2012 for International Application No. PCT/IN2012/000069 (4 pages).

International Preliminary Report on Patentability dated Dec. 1, 2015 for International Patent Application No. PCT/IN2014/000367 (9 pages).

International Preliminary Report on Patentability dated Mar. 1, 2016 for Application No. PCT/IN2014/000551 (7 pages).

International Preliminary Report on Patentability dated Mar. 8, 2016 for International Patent Application No. PCT/IN2014/000584 (10 pages).

Barb et al. (2016) "Pharmacological management on nonalcoholic fatty liver disease" Metabolism Clinical and Experomental 65:1183-1195.

Berger et al. (2005) "PPARs: Therapeutic targets for metabolic disease" Trends in Pharmacological Sciences 26(5): 244-251.

Chou et al. (2013) "Metrelepin: First Global Approval" Drugs 73:989-997.

Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.

FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).

Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.

Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.

Package Insert for ACTOS (pioglitazone) tablets for oral use (2013).

Package Insert for AVANDIA (rosiglitazone maleate) Tablets (2008).

Palomer et al. (2016) "PPARβ/d and lipid metabolism in the heart" Biochemica et Biophysica Acta 1861:1569-1578.

Yessoufou et al. (2010) "Multifaceted roles of peroxisome proliferator-activated receptors (PPARs) at the cellular and whole organism levels" Swiss Medical Weekly 140:w13071.

\* cited by examiner

TREATMENT FOR LIPODYSTROPHY

This application is the U.S. national phase of International Application No. PCT/IN2012/000069 filed 30 Jan. 2012 which designated the U.S. and claims priority to IN 257/MUM/2011 filed 31 Jan. 2011, the entire contents of each of which are hereby incorporated by reference.

FIELD OF THE INVENTION

The present invention is related to the development of therapeutic compound for prevention and treatment of lipodystrophy. In particular the invention relates to the development of therapeutic compound for prevention and treatment of lipodystrophy in HIV-infected patients (LDHIV). Specifically, the present invention further provides a suitable composition useful in the treatment or prevention or alleviation of the symptoms of lipodystrophy in HIV infected patients (LDHIV)

BACKGROUND OF THE INVENTION

Lipodystrophy is a very dreadful disease and has become a major global health problem. It is a disorder of fat metabolism which causes lipohypertrophy, Lipoatrophy and Metabolic abnormalities. Moreover, lipohypertrophy includes the enlargement of dorsocervical fat pad (commonly called "buffalo hump"), expansion of the circumference of the neck by 5-10 cm, hypertrophy occurring in breast, central truncal adiposity resulting from abdominal visceral fat accumulation, symmetric and asymmetric lipomatoses. A rare pattern of lipoaccumulation involves formation of band like lipomatosis tissue symmetrically from the breasts, laterally to the axillae, Suprapubic fat pads (pubic lipomas) and the development of multiple angiolipomas.

Lipoatrophy includes a temporal wasting and loss of subcutaneous fat from the cheeks (buccal fat pad) which produces an emaciated appearance with prominent nasolabial creases. Further subcutaneous tissue is depleted from the arms, shoulders, thighs, and buttocks (peripheral wasting), with prominence of the superficial veins in these sites.

Metabolic abnormalities include augmentation in cholesterol and triglyceride levels and reduced high-density lipoprotein (HDL) cholesterol levels, Insulin resistance, type 2 diabetes mellitus, and lactic academia.

Lipodystrophy is very commonly associated with the HIV patients who are being treated anti-retroviral medicines. Such medicines can include HIV-1 protease inhibitors (PIs), Nucleoside reverse transcriptase inhibitors (NRTIs), Non-nucleoside Reverse Transcriptase Inhibitors (NNRTIs), Fusion Inhibitors, Entry Inhibitors—CCR5 co-receptor antagonist, HIV integrase strand transfer inhibitors etc. These medicines improve the survival of the patient but also produce lipohypertrophy, Lipoatrophy and other Metabolic abnormalities.

HIV-1 protease inhibitors (PIs) appear to be the strongest link to lipodystrophy in HIV-infected patients LDHIV as it inhibits maturation of sterol response element binding proteins (SREBP), which affect intracellular fatty acid and glucose metabolism and adipocyte differentiation (Mallon et al, *J Infect Dis*, 2005). Furthermore, the PIs also down-regulate peroxisome proliferator-activated receptor gamma (PPAR γ), an important nuclear transcription factor that is affected by SREBPs and is necessary for adipocyte differentiation and function and fatty acid metabolism.

Other factors, such as duration of HIV infection, age, and gender, may also contribute to the risk of development of LDHIV. The molecular basis of LDHIV is still remains unknown and no specific therapy is available for LDHIV.

Reverse transcriptase inhibitors (nRTIs) like stavudine, didanosine and zidovudine may cause mitochondrial toxicity by inhibiting mitochondrial DNA polymerase-γ in fat and other tissues and thus interfering with respiratory chain complexes. The result is impaired fatty acid oxidation and intracellular accumulation of triglycerides and lactate In addition, lipodystrophy is also observed in acute HIV infection, lending support to a direct viral role as well. Potential host risk factors include age, sex, and race or ethnicity. Lipodystrophy is more common in older patients; fat accumulation is more common in women and lipoatrophy in men; and non-Hispanic black patients appear to be at lower risk of lipoatrophy. A genetic component is indicated by a recent analysis in AIDS Clinical Trials Group (ACTG), study 5005s, suggesting either predisposition or protection associated with mitochondrial DNA polymorphisms. Hulgan et al, *J Infect Dis*, 2008 describes that patients homozygous for C/C at the HFE187 locus (n=71) had a 0.6-kg and 12.5% loss of limb fat at weeks 48 to 64, with 37 (52%) of the 71 patients diagnosed with clinical lipoatrophy. By comparison, heterozygous patients with HFE187C/G had a 0.2-kg and 6.1% increase in limb fat, with 6 (26%) of 23 patients having clinical lipoatrophy (P<0.05 for all comparisons).

A number of strategies for reducing central obesity have been investigated such as stopping PI treatment but it is not effective. Changes in diet and exercise have produced improvements, but adherence to a regimen of lifestyle change is difficult for most patients. Liposuction may be applied particularly with dorsocervical fat accumulation, i.e., "buffalo hump".

It is evident from the several studies that thiazolidinediones show no change in VAT (Pathogenesis and treatment of lipodystrophy, vol. 16, issue 4, October/November, 2004)

Testosterone replacement to physiologic levels reduces visceral adipose tissue (VAT), total fat, and abdominal fat and improves insulin sensitivity and lipid profile in older, non-HIV-infected men with upper body obesity and low testosterone levels. In a recent study, 88 HIV-infected men with central obesity (waist circumference>100 cm) and low testosterone levels (<400 ng/dL) underwent randomization to testosterone as a transdermal gel at a dose of 10 g daily or placebo for 24 weeks (Bhasin et al, J Clin Endocrinol Metab, 2007). The testosterone group had statistically significant reductions in abdominal fat (−1.5% vs +4.3%), abdominal subcutaneous adipose tissue (SAT) (−7.2% vs +8.1%), trunk fat (−9.9% vs +4.6%), and limb fat (−10.1% vs +3.1%); the latter finding is of potential concern in a population predisposed to lipoatrophy. No statistically significant difference in change in VAT (+0.9% vs +2.3%) was observed, and no statistically significant differences were observed in changes in lipid levels, fasting blood glucose levels, insulin levels, or insulin resistance.

Like testosterone, growth hormone (GH) has fat-oxidizing and lipolytic properties. A substantial proportion of HIV patients with central obesity (approximately 30%-40%) have impaired GH biology, including reduced GH mass secretion, reduced response to GH releasing hormone (GHRH) and free fatty acids, and increased somatostatin tone, which suppresses GH. A number of recent studies have assessed GH treatment in HIV patients with fat accumulation. In 1 study, 325 HIV patients with increased waist: hip ratios and increased VAT measurements received.

Although, the growth hormone (GH) and GH releasing hormone (GHRH) therapies show some promising result as they have fat-oxidizing and lipolytic properties however, there are limitations to their use. They are parenteral therapies and either expensive (rhGH) or not FDA-approved (tesamorelin). Thus far, there is evidence of waning durability of the reduction in VAT after their discontinuation, short-term increases in insulin resistance with rhGH, and small short-term reductions.

Recent research publications have shown the use of two lipid-lowering classes of drugs, statins and fibrates, antiretroviral switching strategies and use of insulin-sensitising drugs as having some beneficial effect on lipodystrophy. However, no single therapy is able to reach desirable clinical end point for HIV associated lipodystrophy.

Hence it is desirable to develop a compound which can overcome the above discussed drawback associated with prior art and develop a therapy for HIV associated lipodystrophy.

Hypolipidemic agents which are PPAR modulators have been disclosed in WO 91/19702, WO 94/01420, WO 94/13650. WO 95/03038, WO 95/17394, WO 96/04260, WO 96/04261, WO 96/33998, WO 97/25042, WO 97/36579, WO 98/28534, WO 99/08501, WO 99/16758, WO 99/19313, WO99/20614, WO 00/23417, WO 00/23445, WO 00/23451, WO 01/53257.

WO 03009841 discloses compounds of the following general formula

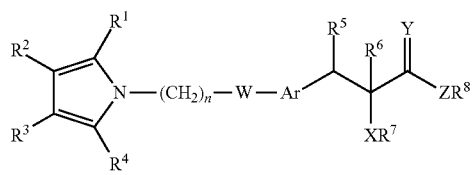

These compounds are reported to be hypolipidaemic agents. This document also discloses sodium and calcium salts of some of the compounds disclosed therein. However, the sodium salts of the compounds of the present invention was difficult to isolate due to rapid degradation while the Calcium salt was poorly absorbed limiting its efficacy and possibility of further development. Further, the calcium salt was also found to degrade on long term storage. It has surprisingly now been found that certain compounds and their selected salts are effective in the treatment of lipohypertrophy, lipoatrophy and metabolic abnormalities in HIV patients.

Embodiments of the Invention

In an embodiment the present invention provides a compound of formula (I) suitable for the treatment and prevention of lipodystrophy.

In an embodiment, the conditions associated with lipodystrophy includes the symptoms of lipohypertrophy, lipoatrophy and other metabolic abnormalities.

In another embodiment, the present invention provides a compound of formula (I) for the treatment and prevention or alleviation of symptoms of lipohypertrophy, lipoatrophy and metabolic abnormalities in HIV patient.

In yet another embodiment the present invention provides the administration of compound of formula (I) and their pharmaceutically acceptable salts alone or in combination with other suitable agents as therapeutic agent for the treatment and prevention alleviation of symptoms of lipodystrophy.

In yet another embodiment the present invention provides a suitable composition comprising the compound of formula (I) or their suitable pharmaceutical compositions suitable for the treatment and prevention alleviation of symptoms of lipodystrophy.

In another embodiment, the present invention provides for certain pharmaceutical salts of compound of formula (I).

SUMMARY OF THE INVENTION

The present invention provides a compound of formula (I) and their pharmaceutically acceptable salts for the prevention and treatment or alleviation of symptoms of lipodystrophy. The present invention provides a compound of formula (I) and their pharmaceutically acceptable salts for the prevention and treatment or alleviation of symptoms of lipodystrophy caused either because of HIV infection or due to treatment with anti-retrovirals. Such anti-retrovirals can include HIV-1 protease inhibitors (PIs), Nucleoside reverse transcriptase inhibitors (NRTIs), Non-nucleoside Reverse Transcriptase Inhibitors (NNRTIs), Fusion Inhibitors, Entry Inhibitors—CCR5 co-receptor antagonist, HIV integrase strand transfer inhibitors etc. or combination therapy involving one or more anti-retrovirals. The compound of formula (I) neutralizes lipohypertrophy, lipoatrophy and metabolic abnormalities in HIV patient. Moreover, the present invention also provides a suitable composition comprising compound of formula (I) useful in the treatment or prevention or alleviation of the symptoms of lipodystrophy in HIV infected patients (LDHIV).

In a further embodiment are disclosed certain new salts corresponding to the compound of formula (I) wherein M represents K or Mg.

DESCRIPTION OF THE INVENTION

The present invention describes compound of formula (I) which is suitable for the treatment of lipodystrophy or HIV associated lipodystrophy.

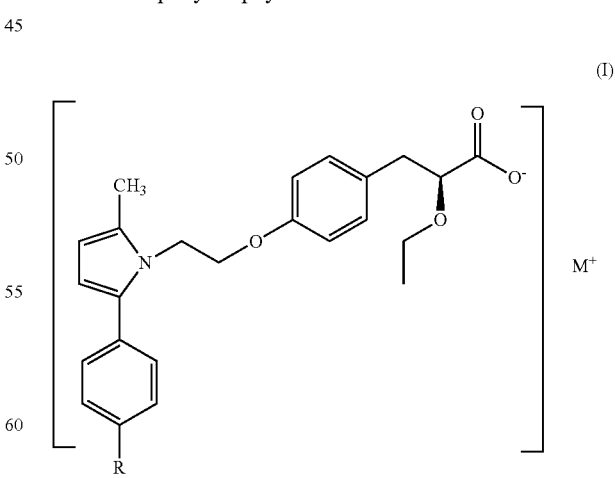

wherein 'R' is selected from hydroxy, hydroxyalkyl, acyl, alkoxy, alkylthio, thioalkyl, aryloxy, arylthio and $M^+$ represents suitable metal cations such as $Na^+$, $K^+$, $Ca^{+2}$, $Mg^{+2}$, and the like.

In a preferred embodiment, 'R' represents thioalkyl, alkoxy or hydroxyalkyl group; In a still preferred embodiment. 'R' represents —SCH$_3$ or —OCH$_3$ group.

In an embodiment is provided suitable pharmaceutical composition for the treatment of lipodystrophy or HIV associated lipodystrophy comprising the compound of formula (I). The pharmaceutical composition of the present invention comprises compound of formula (I) along with suitable excipients as defined hereinafter for the treatment of lipodystrophy or HIV associated lipodystrophy.

In another embodiment, the present invention provides a method of treating a subject suffering from lipodystrophy or HIV associated lipodystrophy which comprises treatment of a patient in need of such therapy, with compound of formula (I) or suitable pharmaceutical compositions containing them.

In a further embodiment the present invention provides use of the compound of formula (I) or their suitable pharmaceutical compositions for the treatment of lipodystrophy or HIV associated lipodystrophy.

In an embodiment the present invention provides certain new salts of compound of formula (Ia)

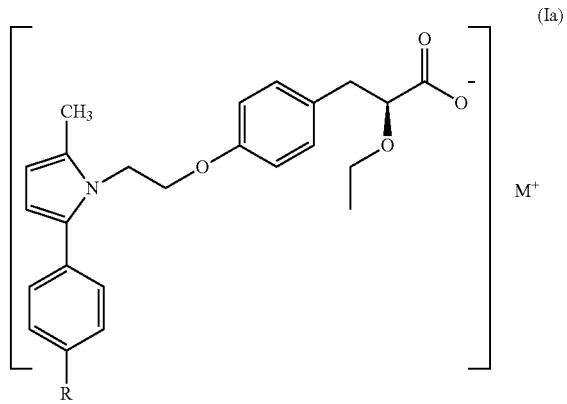

wherein 'R' is selected from hydroxy, hydroxyalkyl, acyl, alkoxy, alkylthio, thioalkyl, aryloxy, arylthio and M$^+$ represents suitable metal cations selected from K$^+$, Mg$^{+2}$.

In a preferred embodiment, 'R' represents thioalkyl and alkoxy or hydroxyalkyl group; In a still preferred embodiment, 'R' represents —SCH$_3$ or —OCH$_3$ group.
In another preferred embodiment, M$^+$ represents Mg$^{+2}$.

The effective amount of the said compound of formula (I) is selected from 1 mg to 500 mg preferably 1 mg to 250 mg and more preferably 4 mg to 50 mg. The compound of formula (I) or its suitable salts is administrated orally, intravenously, parentally in the subject who is in need of treatment.

In an embodiment the compound of formula (I) is useful for the treatment or prevention or alleviation of the symptoms of lipodystrophy. In a preferred embodiment the compound of formula (I) is useful in the treatment or prevention or alleviation of the symptoms of HIV associated lipodystrophy. In such embodiment the Lipodystrophy is a disorder of fat metabolism which causes lipohypertrophy lipoatrophy and metabolic abnormalities.

In an embodiment the compound of formula (1) cure or prevent or alleviate at least one symptoms of lipodystrophy including, but not limited to, acting as an agent for lowering &/or control blood glucose levels, an agent used to control lipid levels, e.g., as an agent used to lower control cholesterol, an antioxidant, an appetite suppressing agent, an anti-obesity agent, a probiotic or an anti-inflammatory agent. In another embodiment the compound of formula (1) cure or prevent or alleviate at least one symptoms of lipodystrophy including, but not limited to triglyceride level, VLDL level and Apo B level in serum. In another embodiment the compound of formula (1) cure or prevent of lipodystrophy by improving at least one of the condition selected from HDL level, Apo A1 level, HOMA of beta cell function derived from c-peptide.

In an embodiment the present invention also provides a suitable pharmaceutical composition of compounds of formula (I) or their derivative. The pharmaceutical composition of the present invention essentially comprises of
  the pharmaceutically active substance;
  a suitable buffering agent;
  a suitable stabilizer;
  optionally with one or more pharmaceutically acceptable excipients.

The suitable stabilizers used in pharmaceutical composition are selected from Polacrilin potassium, Potassium chloride, Sodium stearyl fumarate and preferably selected from Sodium stearyl fumarate. The suitable buffering agent are selected from sodium acetate, ammonia solution, ammonium carbonate, sodium borate, adipic Acid, glycine, monosodium glutamate and preferably selected from ammonia solution.

The pharmaceutically acceptable excipients are selected at least one from carriers, binders, antioxidant agents, disintegrating agents, wetting agents, lubricating agents, chelating agents, surface active agents, and the like.

Diluents include, but are not limited to lactose monohydrate, lactose, polymethacrylates selected from Eudragit, potassium chloride, sulfobutylether b-cyclodextrin, sodium chloride, spray dried lactose, and preferably sulfobutyl ether b-cyclodextrin. Carriers include, but are not limited to lactose, white sugar, sodium chloride, glucose, urea, starch, calcium carbonate and kaolin, crystalline cellulose, and silicic acid. Binders include, but are not limited to carbomers selected from carbopol, gellan, gum Arabic, hydrogenated vegetable oil, polymethacrylates selected from Eudragit, xanthan, lactose and Zein. Antioxidant agents include, but are not limited to, Hypophosphorous acid, Sodium formaldehyde, sodium formaldehyde sulfoxylate, sulfur dioxide, tartaric acid, thymol and methionine. Disintegrating agents include, but are not limited to, bicarbonate salt, chitin, gellan gum, polacrillin potassium and Docusate Sodium. Wetting agents include, but are not limited to, Glycerin, lactose, Docusate Sodium and Glycine, Lubricating agents used include, but are not limited to, Glycerin behenate, hydrogenated vegetable oil, sodium stearyl fumarate and Myristic Acid. Chelating agents include, but are not limited to, Maltol and Pentetic Acid. Surface active agents include but are not limited to, Nonionic surfactant selected from alkyl polyglucosides, cocamide DEA, cocamide MBA, cocamide TEA, decyl maltoside and octyl glucoside; Anionic surfactant selected from arachidic acid and arachidonic acid; Cationic surfactant selected from cetyl trimethylammonium bromide and cetylpyridinium chloride.

In an embodiment the formulation is useful for the treatment or prevention or alleviation of the symptoms of lipodystrophy. In a preferred embodiment the said formulation is useful in the treatment or prevention or alleviation of the symptoms of HIV associated lipodystrophy.

Lipodystrophy is a disorder of fat metabolism which causes lipohypertrophy, lipoatrophy and metabolic abnormalities. Moreover, lipohypertrophy includes the enlargement of dorsocervical fat pad (commonly called "buffalo hump"), expansion of the circumference of the neck by 5-10 cm, hypertrophy occurs in breast, Central truncal adiposity results from abdominal visceral fat accumulation, symmetric and asymmetric lipomatoses. A rare pattern of lipoaccumulation involving bandlike lipomatosis tissue symmetrically from the breasts, laterally to the axillae, suprapubic fat pads (pubic lipomas) and the development of multiple angiolipomas.

Lipoatrophy includes a temporal wasting and loss of subcutaneous fat from the cheeks (buccal fat pad) produces an emaciated appearance with prominent nasolabial creases, subcutaneous tissue is depleted from the arms, shoulders, thighs, and buttocks (peripheral wasting), with prominence of the superficial veins in these sites.

Metabolic abnormalities include augmentation in cholesterol and triglyceride levels and reduced high-density lipoprotein (HDL) cholesterol levels. Insulin resistance, type 2 diabetes mellitus, and lactic academia.

The compounds of the present invention due to their beneficial effect on lipodystrophy, will have beneficial effect on Body fat redistribution (Lioatrophy or Hypertrophy or abnormal distribution), Dyslipidemia, Glucose homeostatis, Pro-inflammatory conditions, impact on morbidity and mortality, impact on quality of life, impact on patient's reported outcomes like self perception etc Moreover, the precise mechanisms underlying this syndrome are not well understood, several hypotheses based on in vitro and human studies may explain the pathogenesis of the changes. Some experts presently believe that HIV type 1 (HIV-1) protease inhibitors (PIs) and nucleoside reverse transcriptase inhibitors (NRTIs), especially stavudine and zidovudine, are implicated as follows:

(i) decreased production of retinoic acid and triglyceride uptake: PIs have a high affinity for the catalytic site of HIV-1 protease, which shares a 60% sequence homology with 2 proteins involved in lipid metabolism, cytoplasmic retinoic acid-binding protein type 1 (CRABP-1) and low-density lipoprotein receptor-related protein (LDLR-RP). Inhibition of CRABP-1 impairs the production of retinoic acid, leading to decreased fat storage and adipocyte apoptosis with the subsequent release of lipids into the circulation. Inhibition of LDLR-RP results in hyperlipidemia secondary to the failure of hepatic and endothelial removal of chylomicrons and triglycerides from the circulation.

(ii) inhibition of mitochondrial DNA (mtDNA) polymerase gamma: NRTIs inhibit mtDNA polymerase gamma, leading to mtDNA depletion, respiratory chain dysfunction, and reduced energy production, which, in turn, causes insulin resistance and secondary dyslipidemia. Interestingly, mtDNA is depleted only at normal oxygen levels— hypoxic adipocytes do not take up triglycerides and are resistant to mtDNA-induced damage, except after treatment with NRTIs.

(iii) inhibition of lipid metabolism: Some PIs, particularly ritonavir, inhibit cytochrome P450 3A, a key enzyme in lipid metabolism.

(iv) prevention of the development of adipocytes: Saquinavir, ritonavir, and nelfinavir (all PIs) directly inhibit the development of adipocytes from stem cells and increase the metabolic destruction of fat in existing adipocytes.

In an embodiment the compound of formula (I) or pharmaceutical composition containing the compound of formula (I) cure or prevent or alleviate at least one symptoms of lipodystrophy including, but not limited to, acting as an agent for lowering &/or an agent used to control blood glucose levels, an agent used to control lipid levels, e.g., as an agent used to lower control cholesterol, an antioxidant, an appetite suppressing agent, an anti-obesity agent, an antibiotic/probiotic or an anti-inflammatory agent. In another embodiment the pharmaceutical composition cure or prevent or alleviate at least one symptoms of lipodystrophy including, but not limited to triglyceride level, VLDL level and Apo B level in serum. In another embodiment the pharmaceutical composition cure or prevent of lipodystrophy by improving at least one of the condition selected from HDL level, Apo A1 level, HOMA of beta cell function derived from c-peptide.

In another embodiment the compounds according to Formula (I) can be used alone or in combination e.g., as an adjunct therapy, with at least one other therapeutic agent. Compound according to formula (I) can be co-administered with a therapeutic agent used to reduce one or more of the symptoms of lipodystrophy including, but not limited to, an agent used to control blood glucose levels, an agent used to control lipid levels, e.g., an agent used to lower control cholesterol, an antioxidant, an appetite suppressing agent, an anti-obesity agent an antibiotic/probiotic or an anti-inflammatory agent. Such combination treatment may be adjunct to anti-retroviral therapy. In a preferred embodiment the compound of formula (I) administrated alone or in combination for the treatment of lipohypertrophy, lipoatrophy and Metabolic abnormalities in HIV patient.

The compound of the present invention when M+ represents K, Mg can be prepared by the processes disclosed herein below along with suitable modifications known to a skilled person.

Example 1

Preparation of (S)-α-Ethoxy-4-[2-[-methyl-5-[4-(methylthio)phenyl]-1H-pyrrol-1-yl]ethoxy]benzene-propanoic acid ethyl ester In a dry, 5 L round bottom flask 2.1 L toluene was taken under nitrogen. To this 366.1 g ethyl (S)-α-2-ethoxy-3-(4-hydroxyphenyl)propionate was added at room temperature.

The reaction mixture was stirred under heating, using Dean-stark apparatus, to remove water azeotropically. The reaction mixture was cooled to 50° C. To this was added 319 g anhydrous potassium carbonate and stirred at 90-92° C. for 1 hr. Cooled to 65° C. and added 500 g 2-(2-methyl-5-(4-(methylthio)phenyl)-1H-pyrrol-1-yl)ethyl methanesulfonate and 22 g tetra butyl ammonium bromide. Reaction mixture was heated to 87-92° C. and stirred for 46 hrs. Cooled to 70-75° C., added 1.5 L toluene, charcoalised using 75 g charcoal and cooled to room temperature. Filtrate washed with alkaline solution, washed with water, dried over sodium sulfate and concentrated under vacuum to obtain (S)-α-Ethoxy-4-[2-[-methyl-5-[4-(methylthio)phenyl]-1H-pyrrol-1-yl]ethoxy]benzene-propanoic acid ethyl ester.

Yield: 650 g, HPLC purity: 84.10%; % Yield 76.0%.

Example 2

Preparation of (S)-α-Ethoxy-4-[2-[-methyl-5-[4-(methylthio)phenyl]-1H-pyrrol-1-yl]ethoxy]benze-nepropanoic acid magnesium salt In a dry, 250 mL round bottom flask 80 mL methanol was taken. To this 20 g (S)-α-ethoxy-4-[2-[-methyl-5-[4-(methylthio)phenyl]-1H-pyrrol-1-yl]ethoxy]benzene-propanoic acid ethyl ester was added at room temperature, under nitrogen. To this 1.89 g sodium hydroxide dissolved in 20 mL water was added and stirred at room temperature for 3 hours to complete hydrolysis. Solvent was removed under reduced pressure. 150 mL water was added to concentrate the material. Impurity was removed by solvent washing. To aqueous layer was added 5 g magnesium acetate tetrahydrate (dissolved in 20 mL water) and stirred with for 15 min. Sticky material was extracted with dichloromethane and subsequently add n-heptane to precipitate (S)-α-ethoxy-4-[2-[-methyl-5-[4-(methylthio)phenyl]-1H-pyrrol-1-yl]ethoxy]benzenepropanoic acid magnesium salt. Solid was filtered, and dried.

Yield: 10.3 g; HPLC Purity: 98.32%; Chiral purity: 97.64%.

Following the process similar to those described in Examples 1 & 2 the following batches of)-α-Ethoxy-4-[2-[-methyl-5-[4-(methylthio)phenyl]-1H-pyrrol-1-yl]ethoxy]benzenepropanoic acid magnesium salt were prepared.

| No. | Batch no. | Input | Output | % Yield | HPLC purity | Chiral purity |
|---|---|---|---|---|---|---|
| 1 | Example 3 | 10 g | 5.02 g | 61.21% | 98.22% | 98.58% |
| 2 | Example 4 | 10 g | 4.97 g | 60.68% | 97.91% | — |
| 3 | Example 5 | 15 g | 7.34 g | 61.94% | 98.20% | — |
| 4 | Example 6 | 15 g | 8.38 g | 67.50% | 99.05% | |
| | Similar reaction carried out using Magnesium chloride | | | | | |
| 5 | Example 7 | 10 g | 6.5 g | 79.25% | 98.53% | 99.32% |
| | Similar reaction carried out using Magnesium sulfate | | | | | |
| 6 | Example 8 | 10 g | 6.8 g | 82.91% | 98.5% | |

The present invention further discloses use of said compound of formula (I) or their suitable pharmaceutical compositions for the treatment of lipohypertrophy, lipoatrophy and metabolic abnormalities in HIV patient.

Example 9

(S)-α-Ethoxy-4-[2-[-methyl-5-[4-(methylthio)phenyl]-1H-pyrrol-1-yl]ethoxy]benzenepropanoic Acid Potassium Salt In a dry, 250 mL round bottom flask 72 mL ethyl acetate was taken. To this 10 g (S)-(−)α-1-phenylethylamine salt of (S)-α-ethoxy-4-[2-[-methyl-5-[4-(methylthio) phenyl]-1H-pyrrol-1-yl]ethoxy]benzene-propanoic acid was added at room temperature and subsequently 50 mL water and 4.8 mL dilute hydrochloric acid (water 1:1:35% HCl) was added and stirred at room temperature till solid was dissolved. Layer was separated and organic layer was washed with water, dried over sodium sulfate and solvent removed. 9.2 g oily mass obtained. To this was added 50 mL methanol and stirred under nitrogen. To this was added 1.81 g potassium t-butoxide and was stirred at room temperature for 15 min. Solvent removed and added n-Hexane. Again n-hexane was removed and added methanol. Solvent removed under vacuum. Hygroscopic material obtained. Dried it under vacuum to get (S)-α-ethoxy-4-[2-[-methyl-5-[4-(methylthio)phenyl]-1H-pyrrol-1-yl]ethoxy]benzenepropanoic acid potassium salt.

Yield—7.6 g, (92.77%), HPLC Purity 98.60%, Chiral purity 99.56%

Example 10

Title of Study: A Prospective, Multi-Centric, Open-Label, Single Arm Study to Evaluate the Safety and Efficacy of 4 mg of compound of formula (I) in Hypertriglyceridemia in HIV Associated Lipodystrophy.

Objectives: The objective of this study was to evaluate the safety and efficacy of 4 mg of compound of formula (I) in hypertriglyceridemia in HIV associated lipodystrophy.

Methodology: This was a prospective, multi-centric, open-label, single arm study to evaluate the safety and efficacy of 4 mg of compound of formula (I) in hypertriglyceridemia in HIV associated lipodystrophy.

After obtaining informed written consent, subjects with hypertriglyceridemia in HIV associated lipodystrophy, on treatment with HAART for at least 18 months and satisfying the inclusion and exclusion criteria were enrolled in the study. The subjects received 4 mg of compound of formula (I) tablet orally, once daily for a period of 12 weeks. During this 12-week program, safety parameters were assessed at weeks 2, 6, and 12 and the efficacy was evaluated at week 6 and 12.

Number of patients: Planned: 50, Analyzed: 50
Test product: Compound of formula (I)
Dose 4 mg
Duration of treatment: 12 weeks
Mode of administration: Oral
Batch number: EMK328
Criteria for evaluation: Efficacy:

The primary efficacy endpoint was to assess the percent change in TG levels from baseline to Week 6 and Week 12. The secondary efficacy endpoint was the assessment of LDL, VLDL, HDL, Non HDL cholesterol, Total cholesterol, Apo A1, Apo B, and C-peptide and fasting insulin for HOMA beta and HOMA IR.

Safety:

Clinical examination and recording of adverse events (AEs) was done on all visits. Electrocardiogram was recorded at screening visit and at Week 12. Urine pregnancy test was conducted at screening visit Haematological examination included haemoglobin, haematocrit, red blood cell (RBC) count, white blood cell (WBC) count with differential (neutrophils, lymphocytes, monocytes, eosinophils and basophils) and platelet count.

Biochemistry tests included AST, ALT, ALP, total bilirubin, serum proteins, total albumin and globulin, γ-GTT, BUN, Serum creatinine, serum uric acid, CPK, and urine R/Ms (including microalbuminuria and ketonuria).

All laboratory parameters were evaluated at enrolment visit (Week 0) and at Weeks 2, 6, and 12.

Statistical Methods

For the efficacy endpoints, treatment effect was evaluated using an analysis of variance (ANOVA) model with factors for baseline and treatment. Treatment effects were estimated using the least-square means (LSM) and 95% confidence intervals (CIs) from the ANOVA model. Statistical significance was defined as a two-sided p-value<0.05. All other secondary endpoints were analyzed using appropriate statistical methods.

For safety analysis the frequency tabulations of abnormal physical examination and abnormal clinical laboratory parameters were presented for each visit. Summary statistics for clinical laboratory parameters and vital signs were presented for each visit. A list of concomitant medications taken during the study period was summarised.

Adverse events were coded using the Medical Dictionary for Regulatory Activities (MedDRA) (Version 14). Adverse events and SAEs were summarized overall, by system organ class (SOC) and by MedDRA preferred term for treatment emergent adverse events (TEAEs). All AEs, including those arising before or after treatment was included in the listings. Separate listings were provided for SAEs and AEs leading to discontinuation from the study.

Study Design

This was a safety and efficacy study to evaluate 4 mg of compound of formula (I) in hypertriglyceridemia in HIV associated lipodystrophy. This was exploratory proof of concept study designed to assess the proof of safety and efficacy in intended population. The results of compound of formula (I) from phase II studies in Dyslipidemia subjects demonstrated that compound of formula (I) 4 mg is well tolerated and effective at once daily dosing. Phase I study demonstrated food significantly affects absorption of compound of formula (I), so drug was recommended to be consumed preferably in fasting condition. Based upon these observations 4 mg once daily in fasted condition was selected for present study Selection of Study Population Inclusion Criteria Subjects who satisfied all of the following criteria were eligible for enrolment in the study:

1. Males and females aged 18-65 years.
2. Confirmed diagnosis of HIV1 and on HAART for at least 18 months.
3. On stable ART regimen for at least 8 weeks prior to inclusion in the study and ART regimen not expected to change in next 3 months.
4. Subjects clinically diagnosed as HIV lipodystrophy (at least 1 moderate or severe lipodystrophy feature identified by doctor and patient, except isolated abdominal obesity)
5. Triglycerides>200 to 500 mg %.
6. CD4 count of >50/mm$^3$
7. Subject who had given informed consent for participation in this trial.

Treatments

Treatments Administered

The study had a single arm. Subjects received 4 mg of compound of formula (I) orally once daily in the morning before breakfast, for a period of 12 weeks.

Identity of Investigational Product(s)

Compound of formula (I) is divalent magnesium salt of carboxylic acid in the form of white, amorphous powder, which is freely soluble in dimethyl sulfoxide, dichloromethane, slightly soluble in methanol and insoluble in water. The drug was supplied as uncoated tablets of 4 mg of the active ingredient.

Supply from batch no EMK328 was used during the study. The study drug was manufactured and packaged in cGMP facility.

Primary Efficacy Variable(s)

The primary efficacy endpoint was to determine the percent change in TG levels from baseline to Week 6 and Week 12.

Secondary Efficacy Variables

The secondary efficacy endpoint was to determine the percent change in LDL, VLDL, HDL, total cholesterol, non-HDL Cholesterol (measured value), Apo A1, and Apo B, C-peptide and fasting insulin for HOMA beta and HOMA IR levels from baseline to Week 6 and Week 12.

Statistical Methods Planned in the Protocol and Determination of Sample Size

Statistical and Analytical Plans

The demographic and baseline characteristics were summarized for compound of formula (I) 4 mg treatment arm. For continuous measurements such as age, the mean, median, standard deviation (SD) and range were tabulated. For categorical measurements such as gender, the frequencies were computed.

Efficacy Analyses:

The primary efficacy variable was the reduction in TG at Week 6 and Week 12 of the treatment period compared with baseline. The change from baseline was determined as the difference between the means for the treatment period (Weeks 6/Weeks 12) and the baseline.

For the efficacy endpoints, treatment effect was evaluated using an analysis of variance (ANOVA) model with factors for baseline and treatment. Treatment effects were estimated using the least-square means (LSM) and 95% confidence intervals (CIs) from the ANOVA model. Statistical significance was defined as a two-sided p-value<0.05. All other secondary endpoints were analyzed using appropriate statistical methods.

Intent-to-treat (ITT) and/or Per Protocol (PP) analysis were carried out for the study. The PP analysis was considered definitive while the ITT analysis was considered supportive during the trial analysis.

Efficacy Results and Tabulations of Individual Patient Data

Analysis of Efficacy

One subject identified as EHT004 in the study: a 35-year-old male, was reported with abnormally low levels of HDL (3.95 mg/L) and LDL (6.25 mg/L) at Visit 1. Though this subject completed the study and was assessable for efficacy, it was decided to exclude this subject from the efficacy analyses. Therefore a total of 49 subjects were analyzed, for efficacy.

Primary Endpoints

The percent change from baseline in serum TG levels at Week 6 and Week 12 following compound of formula (I) 4 mg was statistically significant (−40.98±4.89 and −45.11±3.60, respectively [p-value: <0.0001, each]) (Table 1).

TABLE 1

Analysis of change in Triglyceride (mg/dL) from baseline by visit

| Laboratory Test (Unit) | Visit | | COMPOUND OF FORMULA (I) 4 mg (N = 49) |
|---|---|---|---|
| TG (mg/dL) | Visit 1 | n | 49 |
| | | Mean ± SD | 301.68 ± 86.99 |
| | | Median | 275.45 |
| | | Minimum | 200.10 |
| | | Maximum | 481.42 |
| | Visit 3 (Week 6) | n | 49 |
| | | Mean ± SD | 172.81 ± 106.30 |
| | | Median | 147.68 |
| | | Minimum | 42.61 |
| | | Maximum | 631.08 |
| | | Change from Visit 1 (LS Mean ± SE) | −128.87 ± 14.96 |
| | | p-values | <0.0001 |
| | | % Change from Visit 1 (LS Mean ± SE) | −40.98 ± 4.89 |
| | | p-values | <0.0001 |

TABLE 1-continued

Analysis of change in Triglyceride (mg/dL) from baseline by visit

| Laboratory Test (Unit) | Visit | | COMPOUND OF FORMULA (I) 4 mg (N = 49) |
|---|---|---|---|
| | Visit 4 (Week 12) | n | 49 |
| | | Mean ± SD | 166.97 ± 89.17 |
| | | Median | 145.91 |
| | | Minimum | 46.88 |
| | | Maximum | 387.69 |
| | | Change from Visit 1 (LS Mean ± SE) | −134.71 ± 10.78 |
| | | p-values | <0.0001 |
| | | % Change from Visit 1 (LS Mean ± SE) | −45.11 ± 3.60 |
| | | p-values | <0.0001 |

Key to abbreviations: LSM = least square means; N = number of subjects in the treatment group; n = number of subjects having non-missing baseline and post-baseline values; SD = standard deviation; SE = standard error; TG = triglycerides.
Note:
p-values < 0.05 indicates significant and from ANOVA model Secondary Endpoints
HDL Cholesterol:

There was an increase in the HDL cholesterol levels following administration of compound of formula (I) 4 mg. The percent change from baseline in HDL cholesterol following compound of formula (I) 4 mg at Week 6 and Week 12 was statistically significant (29.92±5.73 and 34.56±6.13, respectively [p-value: <0.0001 each]) (Table 2).

TABLE 2

Analysis of change in HDL Cholesterol (mg/dL) from baseline by visit

| Laboratory Test (Unit) | Visit | | COMPOUND OF FORMULA(I) 4 mg (N = 49) |
|---|---|---|---|
| HDL Cholesterol (mg/dL) | Visit 1 | n | 49 |
| | | Mean ± SD | 35.27 ± 7.85 |
| | | Median | 34.52 |
| | | Minimum | 22.23 |
| | | Maximum | 49.90 |
| | Visit 3 (Week 6) | n | 49 |
| | | Mean ± SD | 44.44 ± 14.04 |
| | | Median | 43.36 |
| | | Minimum | 20.13 |
| | | Maximum | 73.50 |
| | | Change from Visit 1 (LS Mean ± SE) | 9.17 ± 1.99 |
| | | p-values | <0.0001 |
| | | % Change from Visit 1 (LS Mean ± SE) | 29.92 ± 5.73 |
| | | p-values | <0.0001 |
| | Visit 4 (Week 12) | n | 49 |
| | | Mean ± SD | 46.14 ± 14.84 |
| | | Median | 47.70 |
| | | Minimum | 17.61 |
| | | Maximum | 82.89 |
| | | Change from Visit 1 (LS Mean ± SE) | 10.87 ± 2.08 |
| | | p-values | <0.0001 |
| | | % Change from Visit 1 (LS Mean ± SE) | 34.56 ± 6.13 |
| | | p-values | <0.0001 |

Key to abbreviations: LSM = least square means; N = number of subjects in the treatment group; n = number of subjects having non-missing baseline and post-baseline values; SD = standard deviation; SE = standard error; HDL = high density lipoprotein.
Note:
p-values < 0.05 indicates significant and from ANOVA model C-Peptide HOMA of Insulin Resistance:

There was an increase in insulin resistance after treatment with compound of formula (I). The percent change in HOMA IR from baseline following administration of compound of formula (I) 4 mg at Week 6 and Week 12 was statistically significant (27.87±4.22 and 58.29±5.74 respectively [p-value: <0.0001 each]) (Table 3).

TABLE 3

Analyses of change in HOMA of insulin resistance for C-Peptide from baseline by visit

| Laboratory Test (Unit) | Visit | | COMPOUND OF FORMULA(I) 4 mg (N = 49) |
|---|---|---|---|
| Homa of Insulin Resistance for C-Peptide | Visit 1 | n | 49 |
| | | Mean ± SD | 1.59 ± 0.82 |
| | | Median | 1.40 |
| | | Minimum | 0.50 |
| | | Maximum | 3.80 |
| | Visit 3 (Week 6) | n | 49 |
| | | Mean ± SD | 1.86 ± 0.77 |
| | | Median | 1.70 |
| | | Minimum | 0.90 |
| | | Maximum | 3.60 |
| | | Change from Visit 1 (LS Mean ± SE) | 0.27 ± 0.05 |
| | | p-values | <0.0001 |
| | | % Change from Visit 1 (LS Mean ± SE) | 27.87 ± 4.22 |
| | | p-values | <0.0001 |
| | Visit 4 (Week 12) | n | 49 |
| | | Mean ± SD | 2.15 ± 0.62 |
| | | Median | 2.10 |
| | | Minimum | 1.10 |
| | | Maximum | 3.60 |
| | | Change from Visit 1 (LS Mean ± SE) | 0.56 ± 0.05 |
| | | p-values | <0.0001 |
| | | % Change from Visit 1 (LS Mean ± SE) | 58.29 ± 5.74 |
| | | p-values | <0.0001 |

Key to abbreviations: HOMA: homeostasis model assessment, IR: insulin resistance, LSM = least square means; N = number of subjects in the treatment group; n = number of subjects having non-missing baseline and post-baseline values; SD = standard deviation; SE = standard error
Note:
p-values < 0.05 indicates significant and from ANOVA model Insulin (Fasting):

There was an increase in insulin resistance after treatment with compound of formula (I). The percent change in Insulin from baseline following administration of compound of formula (I) 4 mg at Week 6 and Week 12 was statistically significant (23.71±3.55 and 47.10±4.21 respectively [p-value: <0.0001 each]) (Table 4).

TABLE 4

Analyses of change in Insulin (fasting) from baseline by visit

| Laboratory Test (Unit) | Visit | | COMPOUND OF FORMULA (I) 4 mg (N = 49) |
|---|---|---|---|
| Insulin (fasting) μu/mL | Visit 1 | n | 49 |
| | | Mean ± SD | 9.21 ± 6.26 |
| | | Median | 7.40 |
| | | Minimum | 2.65 |
| | | Maximum | 28.06 |
| | Visit 3 (Week 6) | n | 49 |
| | | Mean ± SD | 10.42 ± 5.74 |
| | | Median | 8.35 |
| | | Minimum | 2.14 |
| | | Maximum | 26.82 |
| | | Change from Visit 1 (LS Mean ± SE) | 1.21 ± 0.22 |
| | | p-values | <0.0001 |
| | | % Change from Visit 1 | 23.71 ± 3.55 |

TABLE 4-continued

Analyses of change in Insulin (fasting) from baseline by visit

| Laboratory Test (Unit) | Visit | | COMPOUND OF FORMULA (I) 4 mg (N = 49) |
|---|---|---|---|
| | | (LS Mean ± SE) | |
| | | p-values | <0.0001 |
| | Visit 4 | n | 49 |
| | (Week 12) | Mean ± SD | 11.40 ± 4.45 |
| | | Median | 10.18 |
| | | Minimum | 5.93 |
| | | Maximum | 24.29 |
| | | Change from Visit 1 (LS Mean ± SE) | 2.20 ± 0.21 |
| | | p-values | <0.0001 |
| | | % Change from Visit 1 (LS Mean ± SE) | 47.10 ± 4.21 |
| | | p-values | <0.0001 |

Key to abbreviations: LSM = least square means; N = number of subjects in the treatment group; n = number of subjects having non-missing baseline and post-baseline values; SD = standard deviation; SE = standard error
Note:
p-values < 0.05 indicates significant and from ANOVA model Insulin HOMA of Beta-Cell Function:

There was an increase in HOMA of Beta-cell function derived from Insulin after treatment with compound of formula (I). The percent change in the HOMA of Beta-cell function derived from Insulin from baseline at Week 6 and Week 12 was statistically significant (52.50±14.94 and 45.64±6.22, respectively [p-value: 0.0010 and <0.0001, respectively])(Table 5).

TABLE 5

Analyses of change in HOMA of Beta Cell Function for Insulin from baseline by visit

| Laboratory Test (Unit) | Visit | | COMPOUND OF FORMULA(I) 4 mg (N = 49) |
|---|---|---|---|
| HOMA of Beta Cell Function for Insulin | Visit 1 | n | 48 |
| | | Mean ± SD | 107.82 ± 52.85 |
| | | Median | 97.25 |
| | | Minimum | 10.20 |
| | | Maximum | 234.50 |
| | Visit 3 | n | 49 |
| | (Week 6) | Mean ± SD | 136.41 ± 76.00 |
| | | Median | 116.50 |
| | | Minimum | 34.90 |
| | | Maximum | 348.00 |
| | | Change from Visit 1 (LS Mean ± SE) | 29.55 ± 8.76 |
| | | p-values | 0.0015 |
| | | % Change from Visit 1 (LS Mean ± SE) | 52.50 ± 14.94 |
| | | p-values | 0.0010 |
| | Visit 4 | n | 49 |
| | (Week 12) | Mean ± SD | 137.56 ± 46.11 |
| | | Median | 125.60 |
| | | Minimum | 9.80 |
| | | Maximum | 273.30 |
| | | Change from Visit 1 (LS Mean ± SE) | 30.78 ± 4.25 |
| | | p-values | <0.0001 |
| | | % Change from Visit 1 (LS Mean ± SE) | 45.64 ± 6.22 |
| | | p-values | <0.0001 |

Key to abbreviations: HOMA: homeostasis model assessment, LSM = least square means; N = number of subjects in the treatment group; n = number of subjects having non-missing baseline and post-baseline values; SD = standard deviation; SE = standard error
Note:
p-values < 0.05 indicates significant and from ANOVA model Efficacy Conclusions
Primary Endpoint:
  There was a statistically significant reduction from baseline in serum TG levels at Week 6 and Week 12 following compound of formula (I) 4 mg (percent change of −40.98±4.89 and −45.11±3.60, respectively [p value: <0.0001, each])
Secondary Endpoints:
  There was no statistically significant change in the non-HDL cholesterol levels from baseline following administration of compound of formula (I) 4 mg at Week 6 and Week 12 (p-values: 0.3963 and 0.4646, respectively)
  There was a statistically significant increase in the HDL cholesterol levels from baseline following administration of compound of formula (I) 4 mg at Week 6 and Week 12 (percent change: 29.92±5.73 and 34.56±6.13, respectively [p-value: <0.0001 each]).
  There was a statistically significant increase in the HOMA of Beta-cell function derived from C-peptide from baseline following administration of compound of formula (I) 4 mg at Week 6 and Week 12 (68.25±25.58 and 71.67±16.20, respectively [p-value: 0.0104 and <0.0001, respectively]).
  There was a statistically significant increase in the HOMA of insulin resistance derived from insulin from baseline after treatment with compound of formula (I) at Week 6 and Week 12 (percent change: 29.10±3.94 and 42.65±3.79, respectively [p-value: <0.0001 each]).

Therefore, the compound of the present invention including pharmaceutical compositions containing the same was found to be useful for the treatment of lipohypertrophy, lipoatrophy and Metabolic abnormalities in HIV patients.

We claim:
1. A method for treating lipodystrophy in a subject in need thereof, the method comprising
administering an effective amount of a compound of formula (I)

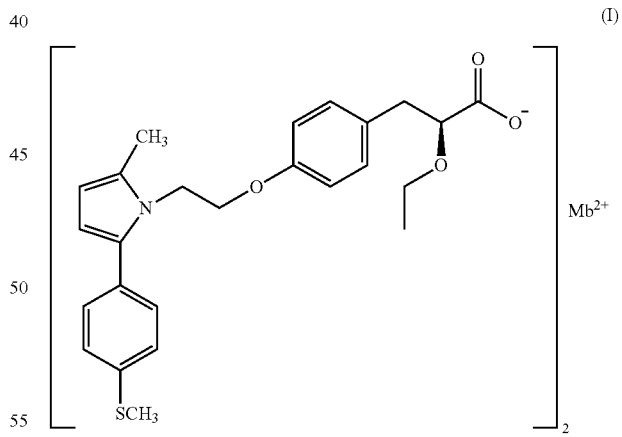

to the subject thereby to treat the lipodystrophy.
2. The method of claim 1, wherein the lipodystrophy is HIV associated lipodystrophy.
3. The method of claim 2, wherein the HIV associated lipodystrophy causes lipohypertrophy, lipoatrophy or a metabolic abnormality.
4. The method of claim 1 further comprising administering to the subject the compound of formula (I) in combination with a second therapeutic agent.

* * * * *

UNITED STATES PATENT AND TRADEMARK OFFICE
CERTIFICATE OF CORRECTION

PATENT NO. : 10,017,470 B2  Page 1 of 1
APPLICATION NO. : 13/978791
DATED : July 10, 2018
INVENTOR(S) : Dhiraj Gambhire et al.

It is certified that error appears in the above-identified patent and that said Letters Patent is hereby corrected as shown below:

In the Claims

In Claim 1, at Column 16, Lines 41-55, replace 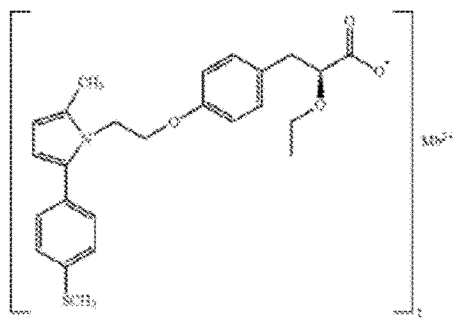 with 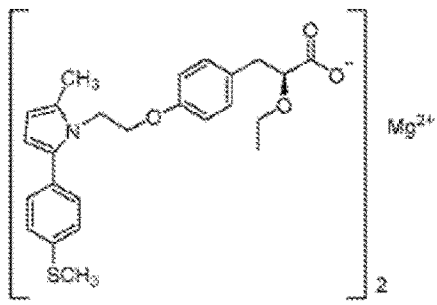.

Signed and Sealed this
Tenth Day of December, 2019

Andrei Iancu
*Director of the United States Patent and Trademark Office*